Figure 1:
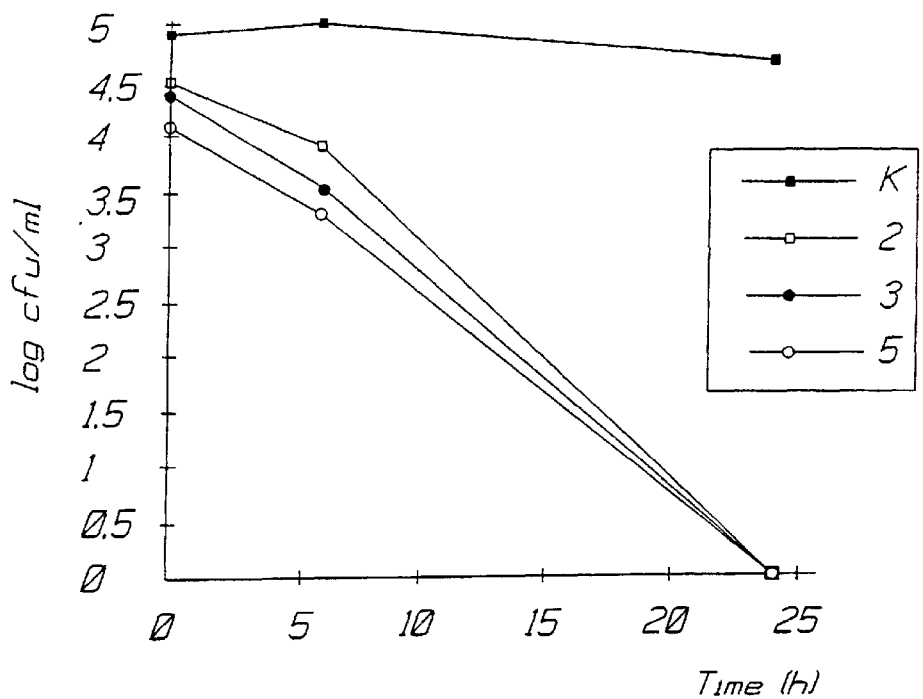

United States Patent [19]
Claesson et al.

[11] Patent Number: 6,149,908
[45] Date of Patent: Nov. 21, 2000

[54] USE OF LACTOPEROXIDASE, A PEROXIDE DONOR AND THIOCYANATE FOR THE MANUFACTURE OF A MEDICAMENT FOR TREATING *HELICOBACTER PYLORI* INFECTION

[75] Inventors: Carl Olof Claesson, Uppsala; Gustaf Lindewald, Vallentuna, both of Sweden

[73] Assignee: Semper AB, Stockholm, Sweden

[21] Appl. No.: 09/117,029

[22] PCT Filed: Jan. 22, 1997

[86] PCT No.: PCT/SE97/00098

§ 371 Date: Jul. 22, 1998

§ 102(e) Date: Jul. 22, 1998

[87] PCT Pub. No.: WO97/26908

PCT Pub. Date: Jul. 31, 1997

[30] Foreign Application Priority Data

Jan. 23, 1996 [SE] Sweden ................................ 9600233

[51] Int. Cl.[7] .................................................. A61K 38/44
[52] U.S. Cl. ........................................................ 424/94.4
[58] Field of Search ............................................ 424/94.4

[56] References Cited

U.S. PATENT DOCUMENTS

| | | | |
|---|---|---|---|
| 4,320,116 | 3/1982 | Bjorck | 424/610 |
| 4,578,265 | 3/1986 | Pellico et al. | 424/94.4 |
| 5,336,494 | 8/1994 | Pellico | 424/94.4 |
| 5,453,284 | 9/1995 | Pellico | 424/94.4 |
| 5,607,681 | 3/1997 | Galley et al. | 424/405 |

FOREIGN PATENT DOCUMENTS

| | | |
|---|---|---|
| 0 387 227 | 11/1990 | European Pat. Off. . |
| 88/02600 | 4/1988 | WIPO . |

OTHER PUBLICATIONS

Dialong Info. Serv., file 5, BIOSIS, Dialog Asccession No. 7195912, Borch et al.—J. Food Prot. 52(9). 1989 (abstract).

*Primary Examiner*—Jean C. Witz
*Attorney, Agent, or Firm*—Larson & Taylor PLC

[57] ABSTRACT

Use of an antibacterial system comprising lactoperoxidase and a peroxide donor for preparing a preparation for prophylactic or therapeutic treatment "in vivo" of an infection caused by the bacteria *Helicobacter pylori* existing in the stomach, which preparation is completed by the presence of thiocyanate in an antibacterial level, and eventually in the presence of lactoferrin. A daily dose for human treatment is 1.2–1.6 grams of the system taken 3 times a day.

7 Claims, 1 Drawing Sheet

USE OF LACTOPEROXIDASE, A PEROXIDE DONOR AND THIOCYANATE FOR THE MANUFACTURE OF A MEDICAMENT FOR TREATING *HELICOBACTER PYLORI* INFECTION

DESCRIPTION

1. Technical field

The present invention relates to the use of a known antibacterial system which is effective against infection of the bacteria *Helicobacter pylori,* which is found in the gastric mucosa and which is related to gastric ulcer.

The object of the present invention is to suggest a possibility of combatting the micro-organism *Helicobacter pylori,* which is a spiral formed, gram negative bacteria existing the human gastric mucosa and also between the cells and intracellulary in the gastric mucosa, which bacteria has been found having a connection to inflammation in ulcus (gastric ulcer disease).

Further characteristics will be evident from the following specification.

2. Background of the Invention

It is known to use the enzyme lactoperoxidase in combination with a thiocyanate and a peroxide donor for extending the freshness of milk. It is also known, as for instance stated in the publication Dialog Information Services, file 5, Biosis, Dialog Accession No 7195912, to treat certain bacteria of the genus Campylobacter with the same lactoperoxidase system by producing antibacterial compositions which are active in the gastro-intestinal system, against diarrhoea and other intestinal diseases. It is shown that the system has an active effect on *Campylobacter jejuni* and *Campylobacter coli.* The patent EP 0 397 227 describes the use of a similar type of lactoperoxidase system for treatment of bacterial Listeria.

The enzyme lactoperoxidase which is used in said compositions is obtained and isolated from bovine milk, or more commonly from dried milk products. It is important, from stability viewpoint, that the enzyme has a pH value of less than 6.5, for instance pH 3.25–6.

Sodium thiocyanate generally has been used as a source of thiocyanate. Alternatively it is possible to use thiocyanate formed from secondary metabolites of plants, preferably within the family Brassicáceae, for instance species of the genus Brassica (types of cabbage like kale) and Sinapis (for instance mustard seed). It is important that the vegetable raw material is heat treated so that existing vegetable peroxidases are made inactive.

As peroxide donor have been used different peroxide producing systems like glucose-glocuseoxidase and solid peroxides, in particular for handling of milk for the purpose of extending the storing qualities thereof. For antibacterial use in the gastro-intestinal canal there have been used solid peroxide donors like alkali percarbonates (sodium percarbonate), earth alkali peroxides (magnesium peroxide) and other solid peroxides (carbamide peroxide), since there are oxygen reducing conditions in the environment of the gastro-intestinal canal.

It is also important that the system according to the invention is stored in inactive state until the moment that the system is to be consumed, especially in the form of powder or tablets, and that it is reactivated in a liquid directly preceding the consumption of same, since the system is active only for a short period of time (for instance between 1 and 24 hours).

It has also shown that an addition of lactoferrin in the system increases the antibacterial effect against *Helicobacter pylori.*

Campylobacter is a bacteria which was formerly considered slightly related to the bacteria which is to-day known as the genus Helicobacter. About 1983–1984 a bacteria Campylobacter was isolated and grown, which bacteria was supposed to cause gastritis and gastric ulcer, eventually even gastric cancer. Said bacteria was first given the name *Campylobacter pyloridis,* but the name was changed in 1987 to *Campylobacter pylori.* A more exact characterisation later proved that said isolated bacteria differs strongly from other bacteria of the type Campylobacter, and since 1989 the bacteria in question has been given a genus of its own, named Helicobacter.

There are great differences between Campylobacter and Helicobacter, both as concerns the way of the respective bacteria of attacking the digestion system and the places of the digestion system where the respective bacteria is attacking. In the publication International Journal of Systematic Bacteriology, October 1989, p. 397–405 is stated that the bacteria which is to-day the genus *Helicobacter pylori* does not actually belong to the genus Campylobacter, and that it differs markedly from Campylobacter for instance as concerns the ultra structure and morphology, cellular fatty acids, menaquinones, growth characteristics and the enzyme capabilities, and in addition thereto in that the antibiotic susceptibility differs from what is the case with Campylobacter.

Several tests have shown that infection by Campylobacter is one of the most common reasons for sporadic enteritis causing inflammation in the first place of the small intestine. Probably the infection starts via a colonisation of the mucosa of the intestine. On the contrary there are no evidence that Campylobacter infects the ventricle mucosa. Normally an infection of Campylobacter does not need a medical treatment. The infection generally passes by itself without any medical treatment. In case there is a serious colitis caused by an infection of Campylobacter, however, the infection is to-day treated by means of antibiotics, for instance Norfloxacin or Erythromycin. Such treatment is quite different from treatment of infections of *Helicobacter pylori,* as will be evident from the following, and no prophylactic or therapeutic treatments of the respective bacteria are compatible.

On the contrary many studies have proved that there is a clear connection between infection by *Helicobacter pylori* and gastritis, gastric mucosa and gastric cancer. Studies have proved that the risque of obtaining an infection increases following ageing, and that 40–50% of the population which is about 50 years of age are infected by *Helicobacter pylori,* which bacteria is, in front of all, found in the mucosa layer of the stomach.

It is obviously the fact that the bacteria Campylobacter solely attacks the external layer of the mucosa, and that the bacteria Campylobacter passes through the oral cavity, the gullet or throat, the stomach and at least those parts of the intestine system located closest to the stomach without causing any infection.

The situation is actually the opposite as concerns the bacteria *Helicobacter pylori,* namely that the bacteria is found in the oral cavity, in the throat and in front of all in the stomach and can cause infection thereof, whereas said bacteria does not attack the intestinal system. The reason therefore probably is that Helicobacter penetrates in between the cells of the stomach and even into the cells of the gastric mucosa and attacks said cells intracellulary, and that the bacteria is capable of protecting itself underneath a thick layer of mucus in the gastric mucosa. Depending on the above mentioned intracellular penetration the bacteria also is protected against the action of antibiotics. Evidence that the bacteria penetrates intracellulary is found for instance in the publication Journal of Clinical Pathology, Vol. 47, p. 699–704, Noach L. A. "Electron microscopy study of association between *Helicobacter pylori* and gastric and duodinal mucosa".

The ability of the bacteria to protect itself under a thick layer of mucus, to present itself intracellulary in the gastric mucosa, and the fact that the acidic environment in the stomach negatively affects certain antimicrobiological substances leads to the conclusion that data concerning elimination "in vitro" of the bacteria *Helicobacter pylori* can not be transferred to an "in vivo" situation.

It is stated in the publication Manual of Clinical Microbiology, 6th edition, ed. P. Murray, E. Baron, M. Pfaller, F. Tenovér, R. Tolken, ASM Press, Washington 1995 that, depending on the inactivity in the acidic environment of the stomach of certain substances, most laboratory tests have indicated that it has not been possible to treat infections of *Helicobacter pylori* "in vivo".

In an article in the Läkartidningen, pages 4268–4271 is also stated:

"*Helicobacter pylori* is susceptible to a large variety of anti microbial substances "in vitro". In spite thereof it is difficult to exterminate the organism. The bacteria are lying well protected in the ventriculus underneath a thick layer of mucus, and there is a poor penetration of antibiotics." Instead thereof such Helicobacter-infections have, with some success, been treated by a so called triple therapy, for instance for 14 days, with a combination of a bismuth salt, Metronidazol and Amoxocillin or Tetracyklin. "However, an increasing resistency against Metronicazol has been reported, and this, in turn, has increased the need for alternative therapies."

*Helicobacter pylori* also are almost unique in that they very rarely cross react serologically with other bacteria. Infection of *Helicobacter pylori* is more commonly existing in developping countries than in industrially developped countries, and this may eventually depend on differencies in hygienic water conditions, since the bacteria survives more than one week in river water.

As far as known to-day *Helicobacter pylori* mainly only can infect the ventricle mucosa, where it gives rise to gastritis, generally in antrum. *Helicobacter pylori* binds to carbon hydrates of the mucosa via a protein. The bacteria thereafter penetrates in between the cells and into the very cells, and by secreting urease, which decomposes urea into ammonia and bicarbonate, the hydrochloric acid in the stomach is neutralised, and the bacteria thereby protects itself against a too low pH. Ammonia is poisoning to the walls of the epithelial cells and changes the structure of mucus, and this makes the bacteria attack the cells intracellulary. Further, the bacteria secretes proteases which decompose proteins and fats and injuries mucus. The patient's reactions on infections give injuries on the adjacent cells but do not cause any damages of the bacteria. Local hormonal disturbances lead to an increased production of acid.

For almost all patients who suffer from ulcus duodeni a gastritis can be traced, which has been induced by the bacteria *Helicobacter pylori*. In fact, 60–80% of the patients who suffer from ulcus ventriculi are infected by *Helicobacter pylori*, but the connection is less than for ulcus duodeni.

As mentioned above infections by *Helicobacter pylori*, so far, have been treated by a triple treatment including treatment with bismuth, Metronidazol and alternatively Amoxocillin or Tetracyklin, or by a treatment comprising a $H_2$-receptor-blocker and two antibiotics. The first mentioned treatment gives an insufficient result and often leads to several adverse effects. The last mentioned treatment gives 60–80% healing.

On the other side there is to-day a restrictive view as regards the use of antibiotics depending on the risque of creations of antibiotic resistant strains.

Therefore, there has been a desire for alternative forms of treatment.

DESCRIPTION OF THE PRESENT INVENTION

So far there has not existed any simple and effective treatment against *Helicobacter pylori* except using the above mentioned triple treatment including treatment with antibiotics.

It is therefore very surprising that it has shown possible to combat infections of *Helicobacter pylori* using a lactoperoxidase system of the initially mentioned type, by using, according to the invention, an antibacterial system comprising lactoperoxidase, a thiocyanate and a peroxide donor for making a preparation for treatment of infections caused by *Helicobacter pylori* present in the oral cavity, in the throat and, in front of all, in the stomach, even against intracellular infection of the gastric mucosa.

It is often possible to treat various bacteria "in vitro", whereas it can be difficult or impossible to treat the same bacteria "in vivo". Helicobacter pylorican be treated by means of a large variety of anti microbial substances "in vitro". In spite thereof it is difficult to exterminate the organism, even using the above mentioned triple treatment by means of antibiotics. Even after such treatment the frequency of refalling ill is high. It is therefore still more surprising that the above mentioned lactoperoxidase system has proved effective for treatment of *Helicobacter pylori* "in vivo", and that a long time treatment is therefore possible without the risque of appearance of resistency against antibiotics.

The present invention provides a pharmaceutical preparation the use of which eliminates the risque of growth of resistant strains.

The present invention has originally been tested "in vitro" in a growth medium as follows: 25 ml Brucella broth, pH 7.4+0.1 ml *H. pylori*, strain NCTC 11637 were mixed in three flasks. The bacteria was allowed to grow in a microaerofile environment for 48 hours. To the respective flask was thereafter added the following after said 48 hours:

1. Check product, no addition;
2. Thiocyanate 35 mg/l;
3. Lactoperoxidase-glucose-glucoseoxidase-thiocyanate. 50 mg/l lactoperoxidase (25 U/mg; 4.5 g/l glucose; 6.1 mg/l glucoseoxidase (200 U/mg); 35 mg/l thiocyanate.

The following data were obtained:

TABLE 1

| Test No | 0 log 10 cfu/ml | 24 hours |
| --- | --- | --- |
| Check | 7.3 | 7.2 |
| 2 | 8.5 | 8.3 |

TABLE 1-continued

| Test No | 0 log 10 cfu/ml | 24 hours |
|---|---|---|
| 3 | 8.3 | 0 |

The results obtained "in vitro" show that a complete extermination of the bacteria *Helicobacter pylori* was obtained between 0 and 24 hours after the system of the invention was added.

The system thereafter also has been tested for finding out the possibility of the system to exterminate the bacteria *Helicobacter pylori* intracellulary.

Test with intracellular extermination of *Helicobacter pylori*

The bacteria is *Helicobacter pylori*, strain M:72, which has been grown in a Brucella broth, pH 6.0 for 2 days.

In the test procedure cells of the human epithelial cell line HEp-1 were infected for 12 hours. Extra cellular bacteria were killed by means of gentamicin (50 mg/l), and the various systems were added. The cells were lysed after 0.6 and 24 hours, see curve K in the diagram of the enclosed FIG. 1. In the figure curves are shown for the following system:

2. Glucoseoxidase+Lactoperoxidase+Glucose+SCN (active thiocyanate);
3. $MgO_2$+Lactoperoxidase+Glucose+SCN;
5. Glucoseoxidase+Lactoperoxidase+Glucose+SCN+ Lactoferrin.

As evident from FIG. 1 all bacteria *Helicobacter pylori* was exterminated in all of the above mentioned systems 2, 3 and 5. This shows that the system enters into the cells and kills all bacteria intracellulary.

It is conspicuous that the active component which is formed by the system, when solved in a liquid, is capable of penetrating into the cells and to kill the bacteria *Helicobacter pylori*.

The system also has been tested "in vivo" in a mouse model and in human bodies:

Mouse studies

In this model the above described "Lactoperoxidase system" has been tested. Further, the same antibacterial system has been tested completed with lactoferrin in order to find out if lactoferrin might potentiate the system.

Method: 30 mice were infected with *Helicobacter pylori*; 7 days after the bacteria was added it was checked that the mice had actually been infected; this was made by growth and verification of *Helicobacter pylori* by PCR-technics.

Thereafter the mice were divided into three groups with 10 mice in each group, a check group and two test groups; the mice in the first one of said test groups were given the above mentioned antibacterial lactoperoxidase system and the mice of the second test group were given the same system completed with lactoferrin.

The antibacterial system comprising lactoperoxidase, glucose, glucoseoxidase and thiocyanate was added. The system was supplied in dried form and was solved in water and was administrated 3 times a day with 0.1 ml per time for 7 days. Thereafter a new analysis was made of the existence of *Helicobacter pylori* of the mice, both by growth in the stomach and by PCR analysis.

Results: The results showed that 8 out of 10 mice in the check group were still colonised with *Helicobacter pylori*. In the first test group, in which the mice were given the antibacterial system, 7 out of 10 mice were growth negative, whereby is means that the bacteria *Helicobacter pylori* had been effectively killed, and in the second test group, in which the mice were given the antibacterial system completed with lactoferrin 8 out of 10 mice were growth negative.

Thus, the results show that the antibacterial system is capable of exterminating the bacteria *Helicobacter pylori* also "in vivo", and this could not have been expected considering the peculiarity of the bacteria to protect itself under a layer of mucus in the gastric mucosa and to exist intracellulary and between the cells in the gastric mucosa.

Human studies

Seven persons were selected to be present in the study. It had been shown, by a so called "urea breath test" that all test persons were infected by *Helicobacter pylori*.

The test persons were actively given the above mentioned antibacterial system for 5 days, and concurrently therewith the persons were given LOSEC® (Astra) as an acid inhibitor. The antibacterial system was included in various products like in a porridge, in milk, in yoghurt and in a chocolate drink. The porridge was taken three times a day, and as a between meal was alternatively taken milk, yoghurt or chocolate drink.

Urea breath tests were made immediately before the antibacterial system was administered and after 5 days during which products containing the antibacterial system had been taken.

Figure 2:
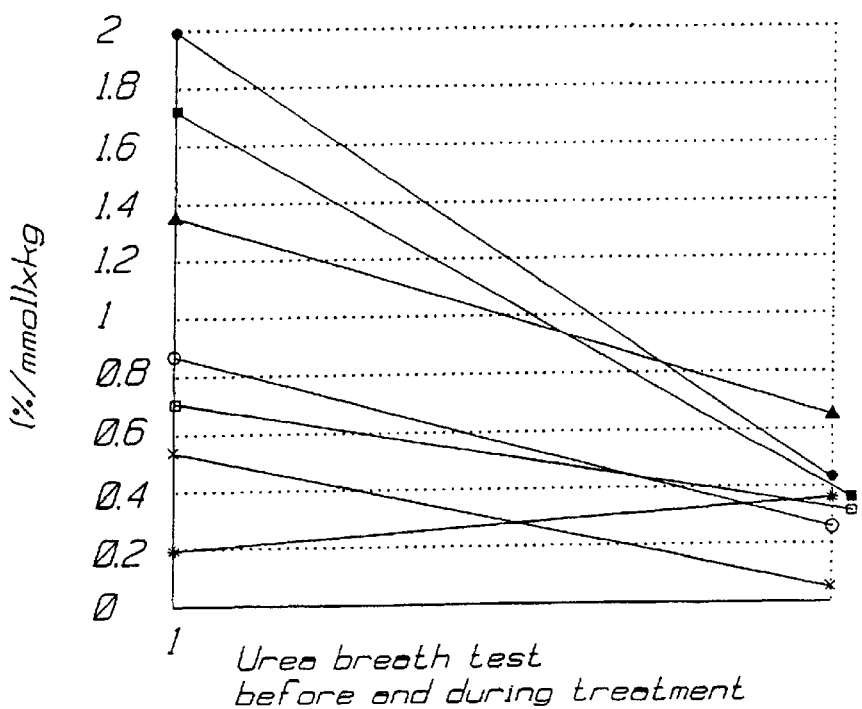

The results are shown in the following table 2 and in the accompanying FIG. 2. The infection by *Helicobacter pylori* had decreased markedly for six of the test persons. The seventh person, for whom no decrease of infection was observed, had a very low level of infection already from the beginning.

TABLE 2

| Person | 1 | 2 | 3 | 4 | 5 | 6 | 7 |
|---|---|---|---|---|---|---|---|
| Before treatment | 1.97 | 1.7 | 1.36 | 0.87 | 0.72 | 0.54 | 0.21 |
| After treatment | 0.45 | 0.42 | 0.67 | 0.29 | 0.34 | 0.06 | 0.36 |

The above indicated results must be considered very sensational and successful considering the fact that it has until now been necessary to make use of a treatment with two antibiotics in combination with an acid secretion inhibitor for exterminating the bacteria *Helicobacter pylori* "in vivo". Still, not even said so far practised very strong treatment has been 100% effective.

The intracellular tests, the mice tests and the human tests thus prove that the antibacterial system comprising lactoperoxidase, glucose, glucoseoxidase and thiocyanate is capable, not only in an "in vitro" system but also in an "in vivo" situation, to exterminate the bacteria *Helicobacter pylori*. It has been shown that this is possible in spite that said bacteria is peculiar in protecting itself under a thick mucus layer in the gastric mucosa and to penetrate intracellulary therein and to protect itself against antibiotics.

Above the lactoperoxidase system has been tested against Helicobacter pylori, strain NCTC 11637. Corresponding tests have been made against other strains of *Helicobacter pylori*, namely VBG H, SVA40, V44-2010, G57, 17874 Vac-A, H:72 and 88-23. The same good results were obtained.

As indicated above in connection to the human studies it is also possible to treat infections of the bacteria *Helicobacter pylori* by means of various preparations like as pure pharmaceutical preparations, but also as food stuffs like in various types of diets. From the latter type it is possible to prepare a wheat diet comprising crushed wheat, skim milk powder, soy meal, calcium caseinate, fats, fibres and emulsifiers to which has been added sodium thiocyanate, a peroxide donor, lactoperoxidase and SCN. It is also possible to make use of various milk products and to add thereto a peroxide donor, and it is likewise possible to make use of a type of cultured milk comprising peroxides producing lactobacilles. By special feeding of the milk producing animals it is also possible to provide an increase of the content of thiocyanate in the milk.

An example of a product is a porridge which is prepared in that a dose of the dried lactoperoxidase system, about 1.2–1.6 gram, is mixed with ¾ dl water and is eaten 3 times a day; an alternative therefore is a drink comprising a portion bag containing about 1.2–1.6 gram of the dried lactoperoxidase system mixed in 2 dl milk or in 2 dl yoghurt and is eaten 3 times a day; a further alternative is a chocolate drink prepared from a dose, likewise of about 1.2–1.6 gram which is mixed in a instant solution chocolate and 1 dl milk and which is eaten as 2 portions a day.

When dosing the pharmaceutical composition comprising the antibacterial system the composition ought to contain so much thiocyanate that the concentration thereof in the gastro-intestinal canal is at least 0.1 mM, and the amount of solid, water soluble peroxide donor or enzyme system should be so great that the concentration thereof gives a hydrogeneperoxide concentration of at least 0.1 mM. The relationship between the peroxide donor and thiocyanate should be less than 4, preferably 1–2. The amount of lactoperoxidase (50 U/mg) is such that the concentration is at least 1 mg/l.

When preparing pharmaceutical preparations comprising an antibacterial system according to the invention said preparation may be in the form of oral preparations like tablets, gelatine capsules or powder. Thereby the selected substances are mixed with a solid powder shaped carrier like lactose, saccharose, sorbitole, mannitole, starch like potato starch, corn starch, amylopectine, cellulose derivate, or gelatine, and with some anti friction substance like magnesium stearate, calcium stearate, polyethyleneglucole waxes and similar stuffs making it possible to make tablets. If it is desired to provide coated tablets for facilitating a peroral administration said tablets can be coated with a polymer which is dissolved by the gastric juice or which allows a diffusion of the active components in the gastric juice. Colourings and taste substances can be added to the polymer.

When preparing gelatine capsules (drop formed, closed, hard or soft capsules) the active compound is mixed with a vegetable oil. The capsules also may contain a granulate of the active components, in combination with solid carriers of the types mentioned above, like lactose, saccharose, sorbitole, mannitole, starch like potato starch, corn starch, amylopectine, cellulose derivate, or gelatine. Further, the granulate may contain decomposition substances for blasting the separate granulate grains thereby providing a quicker releasing and thereby a quicker solving thereof.

Liquid preparations for oral administration can be present in the form of syrups or suspensions, for instance solutions containing 0.2–20% by weight of the above described active substances together with ethanol, glycerol or propylene glycol. The peroxid donor thereby is added in the form of a micro capsuled product for preventing a releasing thereof prior to the administration.

The preparation of tablets is made according to common technics, which technics are well known to the expert, and so are methods for the preparation of granulate for filling of gelatine capsules.

The daily dose of the active system for peroral administraton varies and depends on the type of administration, but as a general rule the dose is between 8–400 mg per day, as concerns the sodium thiocyanate, and 10–500 mg per day as concerns the sodium percarbonate.

The following table 3 gives a general view of the amount of active components suitable for use in various preparation types.

TABLE 3

| Lactoperoxidase (25 U/mg) | 5–150 mg/l |
| Glucose | at least 0.5 g/l* |
| Glucoseoxidase | 2.0–15 mg/l* |
| Thiocyanate | 3–50 mg/l |

*glucose - glucoseoxidase is a peroxide donor. Glucose, however, should be present in such amount that the glocuseoxidase can provide peroxide. An amount of 2.0–15 mg/l glocuseoxidase corresponds to 5–8.5 ml/l glucose. It is also possible to add a solid peroxide donor which gives an equivalent amount of hydrogen peroxide upon reaction. Further a strain of peroxide producing Lactobacillus can be used for generating peroxide.

Lactoperoxidase is added as a pure product, as milk powder, or as a whey product. Glucose oxidase is generally prepared by growing *Aspergillus niger* and isolation thereof from the medium, but a pure natural product like honey can be an alternative. The thiocyanate is added as a salt with sodium or potassium, but it can also be added is the form of a natural product like kale or another Brassicáceae or Sinapis product containing thiocyanate.

PREPARATION EXAMPLE 1

| Granulate of sodium percarbonate containing 10% active oxygen | 100 g |
| Sodium thiocyanate | 40 g |
| Lactoperoxidase (50 U/mg) | 2 g |
| Polyvinylpyrrolidone | 10 g |
| Lactose | 50 g |
| Magnesium stearate | 10 g |

The lactoperoxidase is mixed with lactose and is granulated using a solution of polyvinyl pyrrolidone.

The sodium percarbonate is mixed with the granules of lactoperoxidase. The magnesium stearate is added, whereupon the granulate is formed to tablets.

The tablets have an average weight of 212 mg and are coated with a polymer coating for facilitating the administrating thereof, which coating is dissolved by the gastric juice.

PREPARATION EXAMPLE 2

| Magnesium peroxide | 50 g |
| Sodium thiocyanate | 0.8 g |
| Lactoperoxidase (50 U/mg) | 0.04 g |
| Polyvinylpyrrolidone | 5 g |
| Lactose | 100 g |
| Magnesium stearate | 2 g |

The three active components are granulated separately using polyvinylpyrrolidone as granulation substance. Lactose and magnesium stearate is added, whereupon the mixture is formed to tablets. The obtained tablets (100 tablets) having an average weight of 155 mg are coated with a solution of a polymer which is soluble in the gastric juice.

PREPARATION EXAMPLE 3

| Carbamide peroxide | 50 g |
|---|---|
| Sodium thiocyanate | 20 g |
| Lactoperoxidase | 1 g |
| Lactose | 100 g |
| Steraric acid powder | 2 g |

The carbamide peroxide is granulated using Eudragit S. The lactoperoxidase is mixed with lactose and sodium thiocyanate, and the mixture is granulated by means of Eudragit S. The two granules are mixed and are mixed with the stearic acid powder, and the total mixture is formed to tablets, the average weight of which is 175 mg.

PREPARATION EXAMPLE 4

| I | Sodium percarbonate | 100 g |
|---|---|---|
|  | Mannitol | 20 g |
| II | Sodium thiocyanate | 40 g |
|  | Mannitol | 20 g |
| III | Lactoperoxidase (50 U/mg) | 2 g |
|  | Mannitol | 20 g |

A granulate is prepared from each of I, II and III above using an Eudragit S solution. The combined granulates are mixed with a taste giving substance like sugar, cocoa, microcapsuled lemon aroma, or mixtures thereof. The granulate is dosed by means of a dosing spoon. The granulate is packed in an air tight material.

What is claimed is:

1. A method of treating an individual having a *Helicobacter pylori* infection in the stomach comprising administering to said individual an antibacterial system comprising lactoperoxidase, a peroxide donor and thiocyanate.

2. A method according to claim 1, in which the system is in the form of tablets and is administered perorally.

3. A method according to claim 1, in which the system is in the form of a dry powder which is activated by being dissolved in a liquid immediately preceding the administration thereof.

4. A method according to claim 1, in which the system is in the form of a dry powder which is activated by being dissolved to form a porridge in water, in milk, in a cultured milk product, or in a chocolate drink which is taken in 2 to 3 portions a day.

5. A method according to claim 1, in which the system is further completed by an addition of lactoferrin for potentiating the antibacterial effect.

6. A method according to claim 1, in which the system is administered in a daily dose for human treatment corresponding to 8 to 400 mg thiocyanate or 10 to 500 mg of a peroxide donor.

7. A method according to claim 1, in which the system is administered mixed into a porridge, milk, yogurt, or a chocolate drink taken 3 times a day, each time with a dose of the system comprising 1.2 to 1.6 gram.

* * * * *